(12) United States Patent
Weingaertner et al.

(10) Patent No.: US 11,500,052 B2
(45) Date of Patent: Nov. 15, 2022

(54) SYSTEM AND METHOD FOR PRODUCING TEMPORALLY RESOLVED IMAGES DEPICTING LATE-GADOLINIUM ENHANCEMENT WITH MAGNETIC RESONANCE IMAGING

(71) Applicant: Regents of the University of Minnesota, Minneapolis, MN (US)

(72) Inventors: Sebastian Weingaertner, Minneapolis, MN (US); Mehmet Akcakaya, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/482,098

(22) PCT Filed: Jan. 31, 2018

(86) PCT No.: PCT/US2018/016188
§ 371 (c)(1),
(2) Date: Jul. 30, 2019

(87) PCT Pub. No.: WO2018/144573
PCT Pub. Date: Aug. 9, 2018

(65) Prior Publication Data
US 2020/0041591 A1 Feb. 6, 2020

Related U.S. Application Data

(60) Provisional application No. 62/452,709, filed on Jan. 31, 2017.

(51) Int. Cl.
*G01R 33/48* (2006.01)
*A61B 5/00* (2006.01)
(Continued)

(52) U.S. Cl.
CPC .......... *G01R 33/4818* (2013.01); *A61B 5/349* (2021.01); *A61B 5/7289* (2013.01);
(Continued)

(58) Field of Classification Search
CPC ... A61B 5/0452; A61B 5/7285; A61B 5/7289; G01R 33/4818; G01R 33/5601; G01R 33/5602; G01R 33/5635; G01R 33/5673
See application file for complete search history.

(56) References Cited

U.S. PATENT DOCUMENTS 5,545,992 A * 8/1996 Foo .................... G01R 33/5613
324/309
7,809,426 B2 * 10/2010 Kim ...................... A61B 5/055
600/420

(Continued)

OTHER PUBLICATIONS

Facey. Dummy Scans. University of Ottawa NMR Facility Blog Apr. 7, 2010 [retrieved on Mar. 14, 2018], Retrieved from the internet: URL: http://u-of-o-nmr-facility.blogspot.com/2010/04/dummy-scans.html. 2 pages.

(Continued)

*Primary Examiner* — Steven L Yeninas
(74) *Attorney, Agent, or Firm* — Quarles & Brady LLP

(57) ABSTRACT

Systems and methods for late gadolinium enhancement ("LGE") tissue viability imaging in a dynamic (e.g., temporally-resolved) manner using magnetic resonance imaging ("MRI") are provided. Dynamic LGE images can be generated throughout the entire cardiac cycle at high temporal resolution in a single breath-hold. Dynamic, semi-quantitative longitudinal relaxation maps are acquired and retrospective synthetization of dynamic LGE images is implemented using those semi-quantitative longitudinal relaxation maps.

21 Claims, 4 Drawing Sheets

(51) Int. Cl.
*G01R 33/567* (2006.01)
*G06T 11/00* (2006.01)
*A61B 5/349* (2021.01)

(52) U.S. Cl.
CPC ........ *G01R 33/5673* (2013.01); *G06T 11/008* (2013.01); *G06T 2211/424* (2013.01)

(56) References Cited

U.S. PATENT DOCUMENTS

| | | | | |
|---|---|---|---|---|
| 8,131,338 | B2* | 3/2012 | Kassai | A61B 5/7285 600/410 |
| 8,560,049 | B2* | 10/2013 | Kassai | G01R 33/5615 600/410 |
| 8,700,127 | B2* | 4/2014 | Salerno | G01R 33/5602 600/420 |
| 9,008,753 | B2* | 4/2015 | Messroghli | G01R 33/50 600/413 |
| 9,547,059 | B2* | 1/2017 | Greiser | G01R 33/56 |
| 10,058,249 | B2* | 8/2018 | Slavin | A61B 5/0044 |
| 10,145,927 | B2* | 12/2018 | Voigt | G01R 33/5619 |
| 2009/0245607 | A1* | 10/2009 | Sugiura | G01R 33/4818 382/131 |
| 2009/0302840 | A1* | 12/2009 | Fung | G01R 33/5601 324/309 |
| 2010/0014735 | A1* | 1/2010 | Bi | G01R 33/5635 382/131 |
| 2010/0219829 | A1* | 9/2010 | Rehwald | G01R 33/5613 324/309 |
| 2013/0182930 | A1* | 7/2013 | Trzasko | G06T 11/006 382/131 |
| 2013/0293231 | A1* | 11/2013 | Hirai | A61B 5/055 324/309 |
| 2014/0081123 | A1* | 3/2014 | Korosec | A61B 5/7285 600/413 |
| 2014/0200436 | A1* | 7/2014 | Weingartner | A61B 5/055 600/413 |
| 2015/0038829 | A1* | 2/2015 | Natsuaki | A61B 5/055 600/413 |
| 2015/0123659 | A1* | 5/2015 | Weingartner | A61B 5/055 324/309 |
| 2015/0323630 | A1* | 11/2015 | Weingartner | G01R 33/543 324/309 |
| 2016/0033610 | A1* | 2/2016 | Srinivasan | G01R 33/56325 324/309 |
| 2016/0148378 | A1* | 5/2016 | Salerno | G01R 33/4826 382/131 |
| 2017/0115367 | A1* | 4/2017 | Koestler | G01R 33/56509 |
| 2017/0212195 | A1* | 7/2017 | Rehwald | G01R 33/5602 |
| 2018/0306884 | A1* | 10/2018 | Trzasko | G01R 33/5611 |
| 2019/0235037 | A1* | 8/2019 | Nagashima | G01R 33/385 |

OTHER PUBLICATIONS

International Searching Authority. International Search Report and Written Opinion for application PCT/US2018/016188, dated Mar. 29, 2018. 9 pages.

Matsumoto H, et al. "Late Gadolinium-Enhanced Cardiovascular MRI at End-Systole: Feasibility Study"; Am J Roent 2010; 195(5): 1088-1094.

Moeller S, et al. Multi-scale locally low-rank noise reduction for high-resolution dynamic quantitative cardiac MRI. Conf Proc IEEE Eng Med Biol Soc. Jul. 2017;2017:1473-1476.

Schuster A, et al. End-systolic versus end-diastolic late gadolinium enhanced imaging for the assessment of scar transmurality. Int J Cardiovasc Imaging. 2012;28(4):773-81.

Varga-Szemes A, et al. Myocardial Late Gadolinium Enhancement: Accuracy of T1 Mapping-based Synthetic Inversion-Recovery Imaging. Radiology. 2016;278(2):374-82.

Varga-Szemes A, et al. Effect of inversion time on the precision of myocardial late gadolinium enhancement quantification evaluated with synthetic inversion recovery MR imaging. Eur Radiol. 2017;27(8):3235-43.

Weingärtner S, et al. Temporally resolved parametric assessment of Zmagnetization recovery (TOPAZ): Dynamic myocardial T1 mapping using a cine steady-state look-locker approach. Magnetic resonance in medicine 79.4 (2018): 2087-2100.

* cited by examiner

SYSTEM AND METHOD FOR PRODUCING TEMPORALLY RESOLVED IMAGES DEPICTING LATE-GADOLINIUM ENHANCEMENT WITH MAGNETIC RESONANCE IMAGING

CROSS REFERENCE TO RELATED APPLICATIONS

This application is a U.S. National Stage of PCT Application No. PCT/US2018/016188 filed on Jan. 31, 2018 which claims the benefit of U.S. Provisional Patent Application Ser. No. 62/452,709, filed on Jan. 31, 2017, and entitled "SYSTEM AND METHOD FOR PRODUCING TEMPORALLY RESOLVED IMAGES DEPICTING LATE-GADOLINIUM ENHANCEMENT WITH MAGNETIC RESONANCE IMAGING," which is herein incorporated by reference in its entirety.

STATEMENT REGARDING FEDERALLY SPONSORED RESEARCH

This invention was made with government support under HL111410 and EB015894 awarded by National Institutes of Health. The government has certain rights in the invention.

BACKGROUND

Late gadolinium enhancement ("LGE") is the clinical gold standard for assessment of focal fibrosis/scar and is the most important use of cardiac MRI world-wide. In LGE, scar tissue is visualized as an enhancement 10-20 minutes after contrast injection. Contrast-agent accumulates in the scar-tissue due to diminished washout, and can be depicted by a specific T1-weighted contrast that nulls the signal of the healthy myocardium, which contrasts with the bright scar tissue.

In clinical practice, LGE imaging is performed by acquiring a single inversion recovery image triggered to the diastolic quiescence of the cardiac cycle. The inversion time of this image is chosen to null the healthy myocardium signal. Therefore, LGE viability imaging only provides a single temporal snap-shot of the cardiac cycle.

However, imaging of scar tissue at different cardiac phases in separate scans revealed complementary information on the extent, transmurality, and properties of the necrotic tissue. Acquisition of multiple cardiac-phases in an LGE sequence is so far hindered by differences in the effective inversion time between the cardiac phases. This causes variability in the image contrast between the cardiac phases.

Hence, LGE can currently only be evaluated from a static image. This restricts the obtained information to a single phase, which might obscure scar patterns. Also, motion patterns and dynamic information about the scar and the surrounding tissue (gray-zone) cannot be extracted, thereby narrowing the clinical versatility and value of this widely used technique.

SUMMARY OF THE DISCLOSURE

The present disclosure addresses the aforementioned drawbacks by providing a method for using a magnetic resonance imaging ("MRI") system to produce an image of a subject who has been administered a contrast. The method includes establishing a selected magnetization state in a tissue of the subject using the MRI system, and after the selected magnetization state is established, applying a T1-preparation RF pulse to generate inverted magnetization in the tissue of the subject, which may be partially or completely inverted magnetization. While the inverted magnetization in the tissue of the subject is recovering, and until the selected magnetization state is established again, a data set is acquired at each of a plurality of different cardiac phases by sampling k-space in a k-space segment. The magnetization is then inverted again and more data are acquired for a selected number of inversion recovery periods, such that a plurality of data sets are acquired for each of the plurality of different cardiac phases. Images are reconstructed from the plurality of data sets and maps of a longitudinal relaxation parameter are produced by fitting the images to a signal model. One or more images that depict a late-gadolinium enhancement contrast are then synthesized from the maps of the longitudinal relaxation parameter.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 2A shows an example timing sequence for playing the T1-preparation RF pulses during data acquisition from multiple different cardiac phases. FIG. 2B shows an example of the magnetization recovery curve and the corresponding data acquisition times.

DETAILED DESCRIPTION

Described here are systems and methods for late gadolinium enhancement ("LGE") tissue viability imaging in a dynamic (e.g., temporally-resolved) manner using magnetic resonance imaging ("MRI"). The method described in the present disclosure provides for the generation of dynamic LGE images throughout the entire cardiac cycle at high temporal resolution in a single breath-hold. Dynamic, semi-quantitative longitudinal relaxation maps are acquired and retrospective synthetization of dynamic LGE images is implemented using those semi-quantitative longitudinal relaxation maps.

The method described in the present disclosure implements a pulse sequence that employs an initial T1-preparation RF pulse (e.g., an RF inversion pulse) and subsequent imaging with spoiled gradient echoes for a given number of cardiac phases. This imaging sequence allows for the acquisition of multiple k-space lines per heart-beat and per cardiac phase. Imaging readout is repeated over multiple heart-beats after the T1-preparation RF pulse until a selected magnetization state (e.g., a pulsed or other steady-state, thermal equilibrium, desired level of saturation) is reached. Hence, for each cardiac phase, k-space data are acquired with multiple inversion times. To maintain continuous image excitation, dummy radio frequency ("RF") excitations with no imaging readout may be played after the given number of cardiac phases is acquired and until the detection of a physiological trigger event, which may be an R-wave or other feature in an electrocardiography ("ECG") signal. The entire sequence scheme is repeated multiple times, while shifting the T1-preparation RF pulse throughout the cardiac cycle. This imaging approach allows dense sampling of the apparent longitudinal recovery curve.

Figure 1:
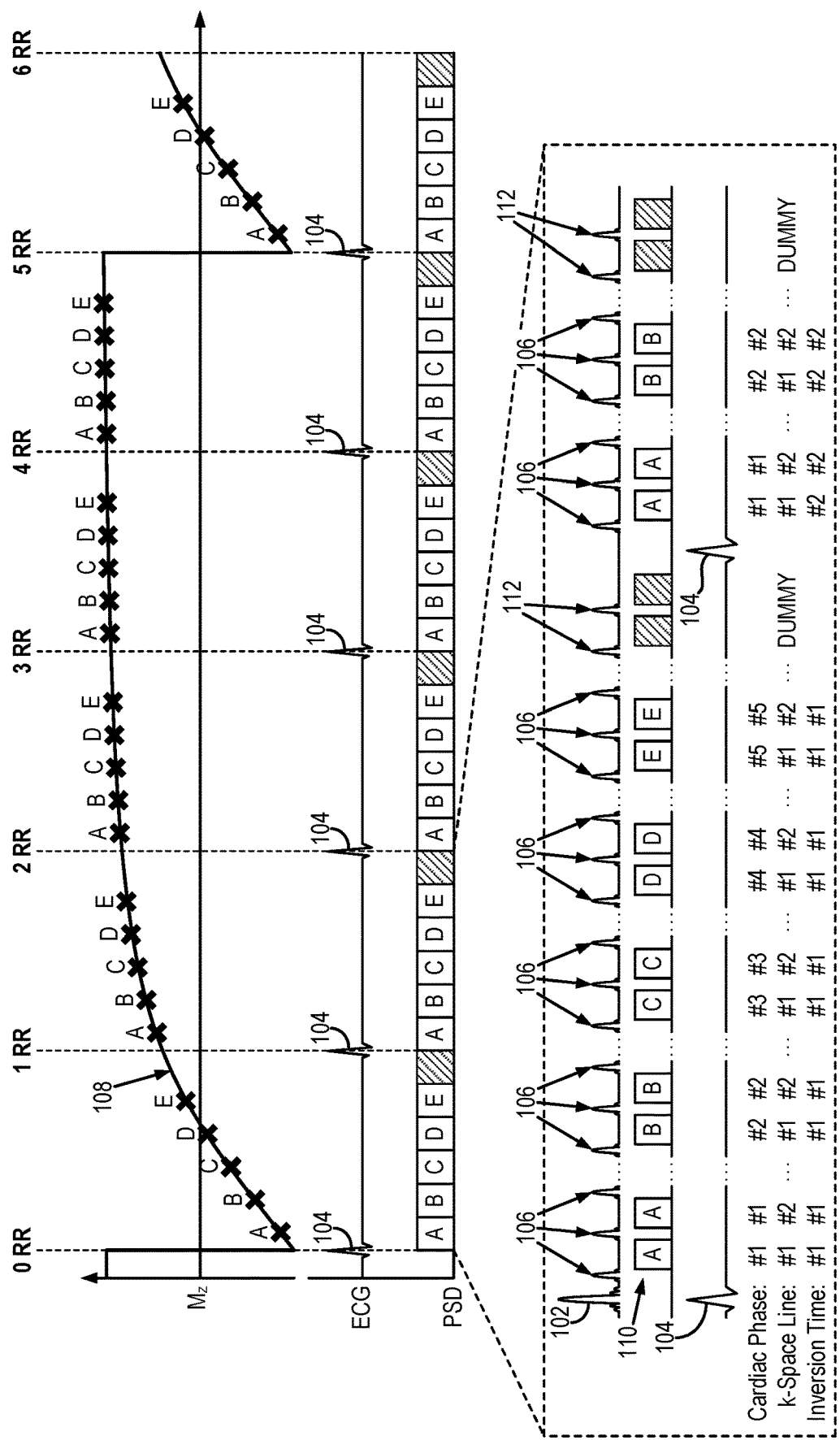
FIG. 1 is an example of a pulse sequence that can be implemented to acquire data from which temporally resolved, semi-quantitative apparent longitudinal relaxation time maps can be produced.

A pulse sequence diagram for an example implementation of the acquisition described in the present disclosure is shown in FIG. 1. In general, imaging is performed with continuous spoiled gradient echoes after magnetization inversion, and is segmented to acquire image information at multiple cardiac phases and multiple inversion times. This approach allows for the generation of semi-quantitative $T_1^*$ maps at each cardiac phase The signal is first driven to a selected magnetization state. In general, the selected magnetization state is a well-defined state, such as a state that can be analytically described in an image reconstruction and that is reproducible from segment-to-segment. As non-limiting examples, the selected magnetization state can be a pulsed or other steady-state, thermal equilibrium, or a desired level of saturation (e.g., total saturation in a particular tissue). In one example implementation, the acquisition begins with continuous fast low-angle shot ("FLASH") imaging pulses to drive magnetization to a pulsed steady-state. As known in the art FLASH imaging pulses may have a flip angle less than 180 degrees, such as in a range of 1-20 degrees.

An initial T1-preparation RF pulse 102 is then applied following, or contemporaneous with, the detection of a physiological trigger event to generate inverted magnetization, which may be partial or complete inverted magnetization. The T1-preparation RF pulse 102 can thus have a flip angle of 180 degrees in some instances, or less than or more than 180 degrees in other instances. For example, the flip angle of the T1-preparation RF pulse 102 can be 170 degrees to provide near complete inversion of magnetization in the selected magnetization state. As one specific and non-limiting example, the magnetization inversion is performed from a steady-state signal using a rectangular hard pulse for the T1-preparation RF pulse 102.

The physiological trigger event can be an R-wave 104, or other signal feature of an electrocardiogram ("ECG") signal measured from the subject being imaged. In other examples, the physiological trigger event can be based on other physiological signals, including pulse oximetry signals, respiratory signals, self-gating signals, and so on.

Following this initial magnetization inversion, FLASH pulses 106 are continuously played to allow for the sampling of an apparent T1 recovery curve 108. The k-space readouts 110 are segmented across several cardiac phases for sufficient temporal resolution. As shown in FIG. 1, data are acquired during five different cardiac phases in each heart-beat, which are labeled as cardiac phases "A," "B," "C," "D," and "E." Multiple inversion times are sampled on the T1 recovery curve 108 until the selected magnetization state (e.g., pulsed steady-state, thermal equilibrium, desired level of saturation) is reached and another magnetization inversion is performed with the application of another T1-preparation RF pulse 102 to sample the next k-space segments. In the example shown in FIG. 1, magnetization inversion is repeated after 5 R-R intervals. This is repeated several times to fill k-space for each cardiac phase at five different inversion-times.

Using the technique described above, a k-space segment is acquired at each cardiac phase for several sample times on the T1 recovery curve 108, where the inversion times for a given cardiac phase are separated by the duration of the R-R interval. As stated above, after multiple heart-beats, the magnetization is driven to the selected magnetization state (e.g., pulsed steady-state, thermal equilibrium, desired level of saturation) and the acquisition of the next series of k-space segments starts with another T1-preparation RF pulse 102 played at the next physiological trigger event (e.g., the next R-wave 104).

To avoid deviation from the recovery curve in the presence of R-R interval variations (or other variations in the time interval between physiological trigger events), dummy pulses 112, with no corresponding signal readout, are played after the acquisition of a pre-determined number of cardiac phases until the detection of the subsequent physiological trigger event (e.g., R-wave 104).

Figure 2A:
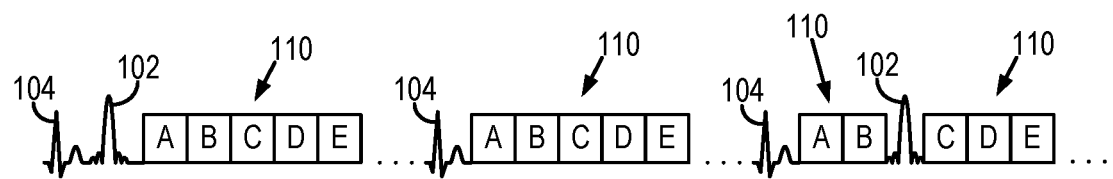
FIGS. 2A and 2B illustrate an example in which data can be acquired using T1-preparation pulses that are repeated at different times within a heartbeat.
Figure 2B:
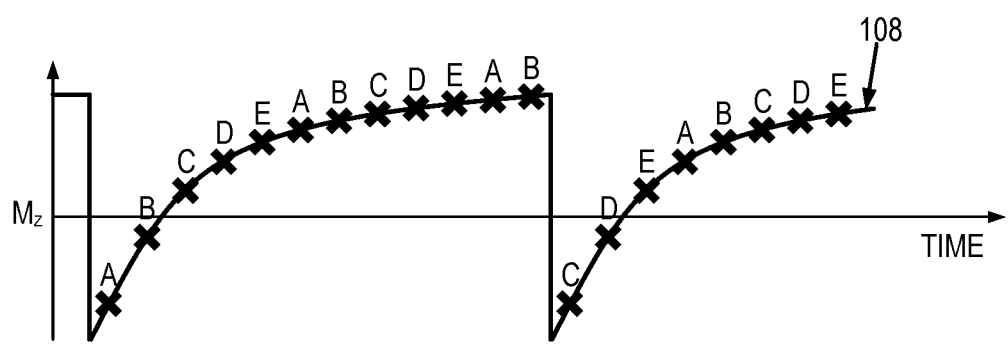

In some embodiments, the T1-preparation RF pulse can implement adiabatic RF pulses, which minimizes the detrimental effect of transmit RF field variability on image quality. The RF excitation pulses used for imaging can be played as spectrally-selective water-excitation pulses to allow for fat suppression around and within the myocardium. Furthermore, because imaging is performed after administering a contrast agent to the subject, the T1 times of the myocardium and blood are significantly lowered compared to measurements in the native state, which accelerates the inverted magnetization's recovery to the selected magnetization state. Thus, multiple different inversion times can be acquired to densely sample the faster-growing T1 recovery curve. As illustrated in FIGS. 2A and 2B, in some implementations data can be acquired from multiple different heart-beats in the same inversion recovery period, and in some instances different T1-preparation RF pulses can be applied at different periods during the cardiac cycle (e.g., between different cardiac phases). By repeating the image acquisition using a varying position of the T1-preparation RF pulse in the cardiac cycle, the sampling density of the inversion recovery curve can be increased.

After data are acquired using the pulse sequence described above, semi-quantitative maps of apparent longitudinal relaxation time are produced based on images reconstructed from the acquired data. These semi-quantitative $T_1^*$ maps can be used to synthesize LGE contrast with a retrospectively chosen, virtual inversion time, which is constant for all cardiac phases. Hence, the methods described in the present disclosure allow for the generation of dynamic cardiac images depicting viability information in a functional manner; that is, as a movie throughout the heart-beat.

The methods described in the present disclosure thus enable imaging with LGE contrast throughout the entire cardiac cycle with high temporal resolution. This can allow for assessment of scar tissue in multiple heart-phases and enables characterization of viability and functional properties of the heart simultaneously.

Figure 3:
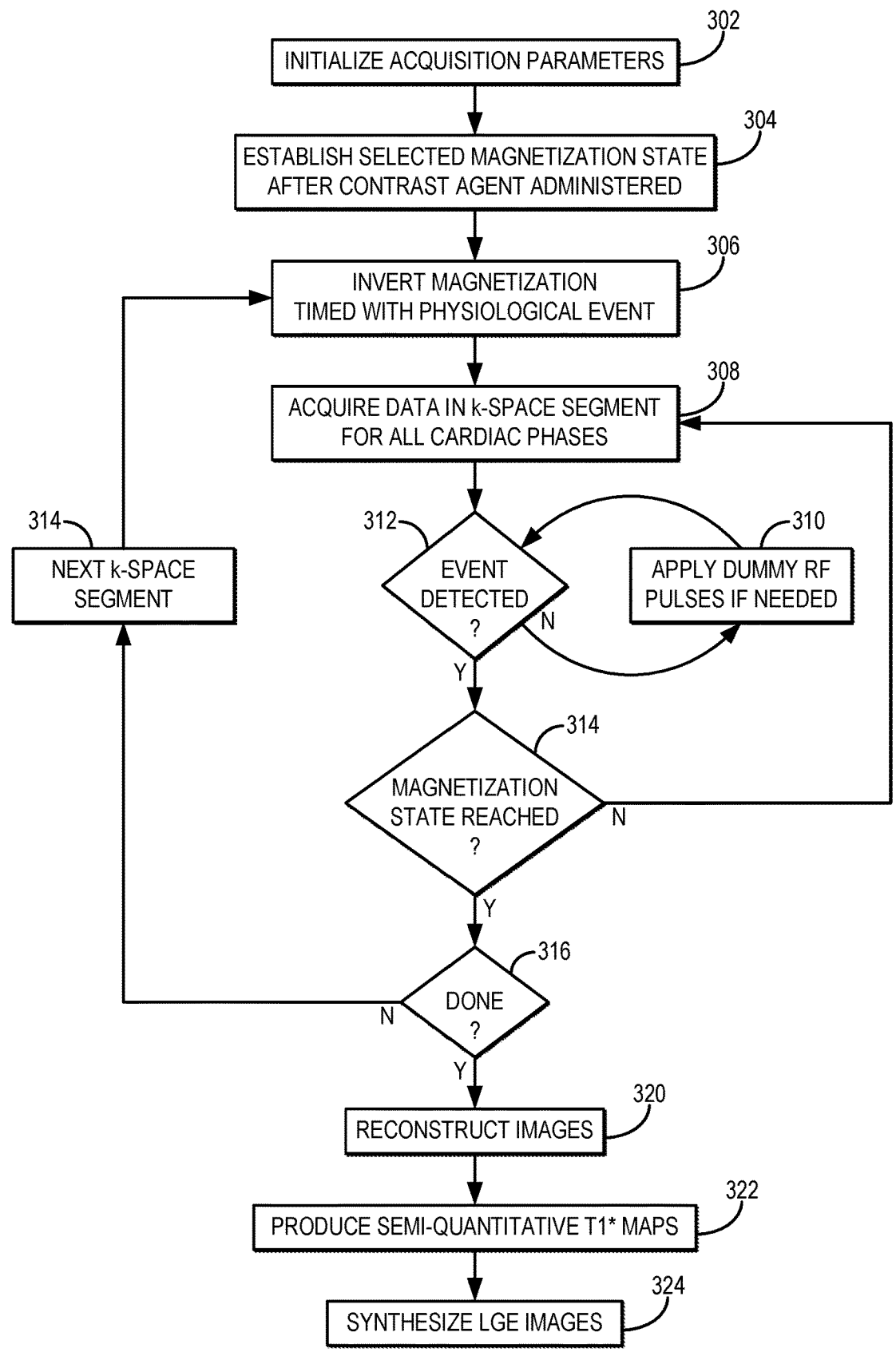
FIG. 3 is a flowchart setting forth the steps of an example method for producing temporally resolved late-gadolinium enhancement images using a magnetic resonance imaging ("MRI") system.

Referring now to FIG. 3, a flowchart is illustrated as setting forth the steps of an example method for producing temporally resolved late-gadolinium enhancement images using an MRI system. The method includes initializing acquisition parameters for the pulse sequence, as indicated at step 302. For instance, acquisition parameters such as flip angle, repetition time, the number of k-space segments (and corresponding number of cardiac phases) to acquire in each inversion recovery period, and the number of inversion recovery periods (and corresponding number of T1-preparation RF pulses to be applied) are selected. In one example, the flip angle may be 3 degrees, the repetition time may be 5 milliseconds, the number of k-space segments to be acquired in each inversion recovery period may be selected from a range of 8-12, and the number of inversion recovery periods may be 5.

The method then includes establishing a selected magnetization state (e.g., a pulsed or other steady-state, thermal equilibrium, a desired level of saturation) in a tissue of a subject to be imaged, as indicated at step 304. For example, steady-stage magnetization can be established by applying a series of continuous RF pulses with a low flip angle (e.g., continuous FLASH imaging pulses).

After the selected magnetization state is established, the magnetization is inverted, as indicated at step 306, to generate inverted magnetization, which may be fully or partially inverted. For example, the magnetization is inverted by applying a T1-preparation RF pulse with the MRI system. The magnetization inversion is timed to be contemporaneous with, or to otherwise follow, the detection of a physiological trigger event measured from the subject. As one example, the physiological trigger event can be the detection of an R-wave, or other features, in an ECG signal measured from the subject. In other examples, the physiological trigger event can be measured from other physiological signals, such as pulse oximetry signals, respiratory signals, self-gating signals, and so on.

While the magnetization is recovering, the T1 recovery curve is sampled by acquiring data in multiple different k-space segments at a corresponding multiple different cardiac phases. Thus, data are acquired in a k-space segment across multiple cardiac phases, as indicated at step 308. As an example, the data are acquired using a series of spoiled gradient acquisitions with a low flip angle (e.g., using a FLASH acquisition scheme).

After the selected number of acquisitions has been performed for the k-space segment and the cardiac phases, dummy RF pulses with no corresponding signal acquisition may be played out, as indicated at step 310, until the detection of a physiological trigger event, as indicated at decision block 312. As mentioned above, the physiological trigger event may be the detection of an R-wave or other feature in an ECG signal measured from the subject. In other examples, the physiological trigger event can be based on other physiological signals, including pulse oximetry signals, respiratory signals, self-gating signals, and so on.

After detection of this physiological trigger event, a determination is made as to whether the selected magnetization state has been established again, as indicated at decision block 314. If not, then data are acquired in the same k-space segment for the next set of cardiac phases. Because these data are acquired at different time points in the magnetization recovery curve, they will be representative of different inversion times.

When the selected magnetization state is established again, as determined at decision block 314, a determination is made as to whether a stopping criterion has been established, as determined at decision block 316. As one example, the stopping criterion can be based on whether the selected number of k-space segments have been acquired across the selected number of inversion recovery periods. If the stopping criterion has not yet been satisfied, the next k-space segment is selected at step 318 and the magnetization is inverted again at step 306. Data for the next k-space segment are then acquired over multiple cardiac phases while the magnetization recovers back to the selected magnetization state, as described above. In some instances, the image acquisition can be repeated multiple times by playing the T1-preparation RF pulse at a different times within the heartbeat, as shown in FIGS. 2A and 2B.

After data are acquired for all selected k-space segments and cardiac phases across the selected number of inversion recovery periods, images are reconstructed from the acquired data, as indicated at step 320. Based on the reconstructed images, semi-quantitative $T_1^*$ maps can be produced, as indicated at step 322. In general, the $T_1^*$ maps can be generated by fitting the reconstructed images to an appropriate signal model. As one example, when contiguous FLASH pulses are used for the data acquisition, the magnetization signal can be described by a parametric inversion recovery model, $$M_z(t) = M_{SS} - (M_{SS} - M_z(0)) \cdot e^{-\frac{t}{T_1^*}} ; \qquad (1)$$

where $M_z(t)$ is the longitudinal magnetization at a time, t; $M_{SS}$ is the magnetization in the steady-state; $M_z(0)$ is the initial longitudinal magnetization following inversion; and $T_1^*$ is an apparent longitudinal relaxation time, which is a function of the flip-angle, $\alpha$, and the repetition time ("TR"):

$$T_1^* = \left(\frac{1}{T_1} - \frac{1}{TR} \cdot \log(\cos(\alpha))\right)^{-1}. \qquad (2)$$

When the magnetization inversion is performed from the steady-state signal using an adiabatic inversion, the initial signal can be approximated as, $$M_z(0) = -M_{SS} \qquad (3);$$

which leads to the following magnetization:

$$M_z(t) = M_{SS}\left(1 - 2 \cdot e^{-\frac{t}{T_1^*}}\right). \qquad (4)$$

Thus, parameter quantification can be performed using a two-parameter least square fit, $$\left(\hat{A}, \hat{T_1^*}\right) = \arg\min_{A, T_1^*} \sum_k \left\|S(t_k) - A \cdot \left(1 - 2 \cdot e^{-\frac{t_k}{T_1^*}}\right)\right\|^2; \qquad (5)$$

where $t_k$ denotes the inversion time of the $k^{th}$ image and $S(t_k)$ is the corresponding signal for a given pixel location.

The semi-quantitative $T_1^*$ maps can then be used to synthesize LGE images at any point during the cardiac cycle, as indicated at step 324. For example, the image intensity of a voxel in the synthesized LGE image at any cardiac phase can be described as, $$I(t_{inv}) = A \cdot \left(1 - 2 \cdot e^{-\frac{t_{inv}}{T_1^*}}\right); \qquad (6)$$

where A and $T_1^*$ described the parameters as obtained from the two-parameter fit described above, and $t_{inv}$ is a virtual, retrospectively selected inversion time, which can be adapted to provide optimal contrast in the synthesized images. Images synthesized as described above can exhibit a signed signal polarity, which can help differentiate between tissues with shortened T1 times (e.g., scar tissue) and tissues with very long T1 times.

Although a conventional image reconstruction can be used in step 320, in some implementations a multi-scale locally low-rank noise reduction can be used in an iterative reconstruction algorithm.

As one example, for a fixed pixel location, the LLR approach can extract patches of size $m_1 \times m_2$, whose top left corner is at that pixel throughout the series of N images. These patches, which are positioned at the given pixel, are then vectorized and these vectors are put together to form a Casorati matrix, whose dimension is $m_1 m_2 \times N$. Due to redundancies in the image series that acquire the same anatomy over time or through contrast changes, this Casorati matrix can be represented accurately by a low-rank matrix, which can be enforced via singular value thresholding. The process is then repeated for other pixels to cover the whole image in-plane.

As another example, alternating between enforcing consistency with the acquired k-space data, and the LLR regularization of the images is avoided, while exploiting noise information that can be derived from the raw k-space data. To this end, an image reconstruction, which may be a parallel imaging reconstruction, in SNR units is performed. This initial reconstruction allows for the underlying noise distribution in the reconstruction to correspond a normal distribution. Following the extraction of the relevant local patches into a Casorati matrix, singular value thresholding can be performed. Because the reconstruction is in SNR units, the threshold parameter can be calculated analytically from the singular value distribution of a Gaussian random matrix, which follows a Marchenko-Pastur distribution, thereby eliminating the need for a heuristic parameter selection process. This process can be repeated for overlapping patches to avoid blocking artifacts, where patches are shifted by half a patch size in each direction.

A multi-scale denoising approach is then implemented in this example. In general, multi-scale approaches can include changing patch sizes or using a quad-tree structure. As one example, multiple patch sizes, $m_1^{(k)} \times m_2^{(k)}$, with their corresponding regularization parameters, $\lambda_{MP}^{(k)}$, can be used. As noted, the regularization parameters can be derived from a Marchenko-Pastur distribution, but in other examples different regularization parameters can also be used. Letting $R_{m,n}^p$ be the operator that extracts the m×n block whose top-left corner is at pixel location, p, into a Casorati matrix, and letting Y be the noisy image series, the following problem can be solved, $$\min_X \sum_p \sum_k \left[ \frac{1}{2} \left\| R_{m_1^{(k)}, m_2^{(k)}}^p (Y - X) \right\|_F^2 + \lambda_{MP}^{(k)} \left\| R_{m_1^{(k)}, m_2^{(k)}}^p (X) \right\|_* \right]. \quad (7)$$

As one example, the problem in Eqn. (7) can be solved using a projection onto convex sets ("POCS") technique.

As still another example, a locally low-rank tensor regularization can be used on local patches to enable the reconstruction of high-resolution quantitative images. The data acquired using the data acquisition techniques described in the present disclosure can be treated as a four-dimensional data structure, m(x,y,t,c), where (x,y) is the discrete spatial location, t is the cardiac phase, and c is different $T_1$ contrasts. Data acquired in k-space is given as, $$y(t,c) = E_{t,c}(m(x,y,t,c)) + n(t,c) \quad (8);$$

for t=1, ..., T and c=1, ... C, and where $E_{t,c}: \mathbb{C}^{M \times N} \to \mathbb{C}^P$ is the measurement system, including a partial Fourier matrix and the sensitivities of the receiver coil array, if one is used; $n(t,c) \in \mathbb{C}^P$ is the measurement noise; t is the cardiac phase; c is the contrast weighting; and x and y are the discrete spatial locations.

The four-dimensional data set, m (x,y,t,c) can be naturally represented as a fourth-order tensor, $$m = \sum_{r=1}^R a_r \otimes b_r \otimes c_r \otimes d_r \Leftrightarrow m(i,j,k,l) = \sum_{r=1}^R a_r(i) b_r(j) c_r(k) d_r(l); \quad (9)$$

where $\otimes$ represents the outer product, and R represents the rank of the tensor, m, the minimum number of rank one tensors needed to synthesize m as their sum. Finding the rank of a tensor is an NP-hard problem, with an upper bound given by min{MNT,MNC,MTC,NTC}.

Tucker and PARAFAC decompositions are two main approaches in low-rank tensor approximation. PARAFAC decomposition uniquely factorizes a tensor into a sum of rank one tensors, whereas Tucker decomposition factorizes a tensor into a core tensor multiplied by a matrix along each mode. Of these two approaches, the Tucker model is typically used for compression applications, and applied to the context of the image reconstruction problem presented here would include choosing four mode ranks, as it assumes low rank in each mode. PARAFAC is a direct low-rank decomposition that is mostly used for latent signal estimation, and uses a single tensor rank parameter.

In some applications of tensor regularization to MRI, the regularization can be performed globally. A global approach is suboptimal, however, because the imaging field-of-view often contains multiple structures with different functional and contrast properties. For instance, the chest wall and back contain stationary tissue that is high in fat, which has a very short T1. The heart muscle (myocardium), on the other hand, contracts and expands substantially through the cardiac cycle and has a longer T1. The blood pools also move and have even longer T1. Thus, it is hard to capture all the information in a few rank-1 components.

When using the methods described in the present disclosure, a tensor regularization can be implemented with small local patches in the spatial domain, which are modeled as low-rank tensors. This technique increases the likelihood that a patch will contain only tissue types that are related in function and contrast, instead of containing a large number of tissue types with varying properties.

As one example of a low-rank tensor-based regularization, images are first reconstructed, which may be performed using conventional or parallel image reconstruction. For instance, parallel imaging can be applied to each of a number of contrast weightings (e.g., C=5) and cardiac phases (e.g., T=11) individually to avoid or otherwise mitigate temporal blurring, contrast blurring, or both, in the reconstructed images. In other instances, a regularized image reconstruction can be implemented, where the regularization is provided by the tensor regularization now described.

Tensor regularization can be implemented to reduce the noise amplification due to the image reconstruction (e.g., the noise amplification due to linear parallel imaging reconstruction) in post-processing. One example of low-rank tensor factorization for noise reduction of a four-dimensional noisy tensor, X, can be carried out by solving the following problem:

$$\min_{\{a_r,b_r,c_r,d_r\}_{r=1}^R} \left\| X - \sum_{r=1}^R a_r \otimes b_r \otimes c_r \otimes d_r \right\|_F^2. \tag{10}$$

In some implementations, instead of solving the above least squares problem, which is non-convex, an alternating least squares ("ALS") approach can be used. In such instances, ALS solves for $\{a_r\}$ by fixing $\{b_r\}$, $\{c_r\}$, and $\{d_r\}$ so that the problem becomes (conditionally) linear. The procedure can then be repeated for the other components until a stopping criterion is met.

Figure 4:
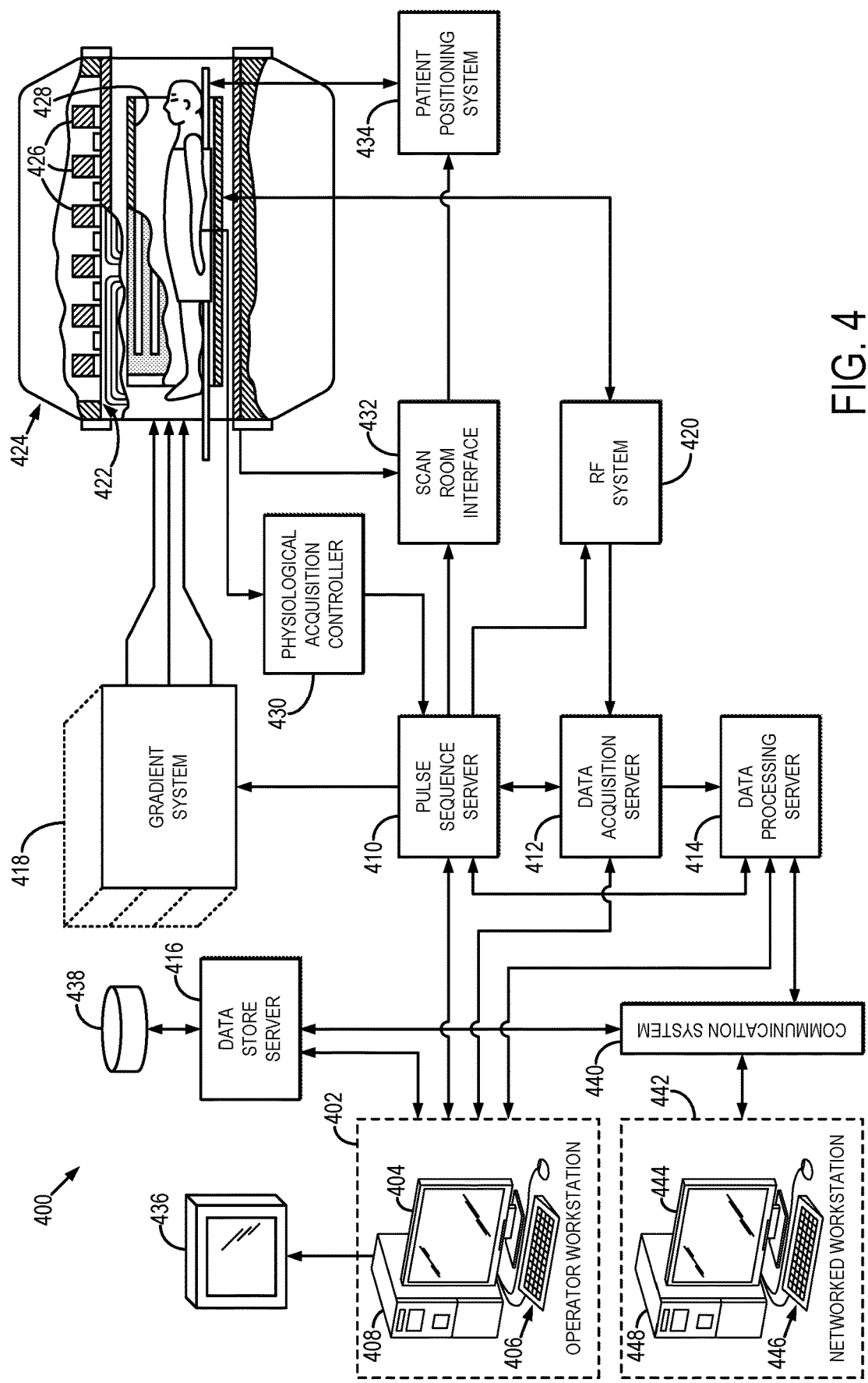
FIG. 4 is a block diagram of an example MRI system that can implement the methods described in the present disclosure.

Referring particularly now to FIG. 4, an example of an MRI system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \tag{11};$$

and the phase of the received magnetic resonance signal may also be determined according to the following relationship:

$$\varphi = \tan^{-1}\left(\frac{Q}{I}\right). \tag{12}$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

The present disclosure has described one or more preferred embodiments, and it should be appreciated that many equivalents, alternatives, variations, and modifications, aside from those expressly stated, are possible and within the scope of the invention.

The invention claimed is:

1. A method for using a magnetic resonance imaging (MRI) system to produce an image of a subject who has been administered a contrast, the steps of the method comprising:
   (a) establishing a selected magnetization state in a tissue of the subject using the MRI system;
   (b) after the selected magnetization state is established, applying a T1-preparation radio frequency (RF) pulse to generate inverted magnetization in the tissue of the subject;
   (c) while the inverted magnetization in the tissue of the subject is recovering and until the selected magnetization state is established again, acquiring a data set at each of a plurality of different cardiac phases over multiple different R-R intervals by sampling k-space, wherein for each different R-R interval, after acquiring data for each data set, applying a selected number of dummy RF pulses until a physiological trigger event is detected;
   (d) repeating steps (b) and (c) for a selected number of inversion recovery periods such that a plurality of data sets are acquired for each of the plurality of different cardiac phases;
   (e) reconstructing images from the plurality of data sets;
   (f) producing maps of a longitudinal relaxation parameter by fitting the images to a signal model; and
   (g) synthesizing an image that depicts a late-gadolinium enhancement contrast from the maps of the longitudinal relaxation parameter.

2. The method as recited in claim 1, wherein the T1-preparation RF pulse is applied at a time based on a detection of a physiological trigger event measured from the subject.

3. The method as recited in claim 2, wherein the physiological trigger event is an occurrence of an R-wave in an electrocardiograph (ECG) signal measured from the subject.

4. The method as recited in claim 3, wherein the T1-preparation RF pulse is applied when the R-wave in the ECG signal is detected.

5. The method as recited in claim 1, wherein the selected magnetization state is a pulsed steady-state and is established in step (a) by applying a series of continuous RF pulses to the tissue of the subject.

6. The method as recited in claim 5, wherein the series of continuous RF pulses comprises RF pulses having a flip angle less than 180 degrees.

7. The method as recited in claim 6, wherein the series of continuous RF pulses comprises RF pulses having a flip angle in a range of 1 to 20 degrees.

8. The method as recited in claim 1, wherein data in each data set are acquired by sampling k-space in the k-space segment using a data acquisition comprising a series of continuous RF pulses and a spoiled gradient readout.

9. The method as recited in claim 8, wherein the series of continuous RF pulses comprises RF pulses having a flip angle less than 180 degrees.

10. The method as recited in claim 9, wherein the series of continuous RF pulses comprises RF pulses having a flip angle in a range of 1 to 20 degrees.

11. The method as recited in claim 1, wherein the physiological trigger event is an occurrence of an R-wave in an electrocardiograph (ECG) signal measured from the subject.

12. The method as recited in claim 1, wherein no data are acquired in response to the dummy RF pulses.

13. The method as recited in claim 1, wherein step (c) includes acquiring each data set for each of the plurality of different cardiac phases by sampling k-space in a different k-space segment.

14. The method as recited in claim 1, wherein step (g) includes synthesizing the image for an arbitrary inversion time.

15. The method as recited in claim 1, wherein step (g) includes synthesizing a plurality of images each having a different late-gadolinium enhancement contrast associated with a different retrospectively selected inversion time.

16. The method as recited in claim 1, wherein step (g) includes synthesizing a plurality of images each having a same late-gadolinium enhancement contrast associated with a single retrospectively selected inversion time and the plurality of images are temporally resolved images.

17. The method as recited in claim 1, wherein the T1-preparation RF pulse is an RF inversion pulse.

18. The method as recited in claim 1, wherein the T1-preparation RF pulse is an adiabatic T1-preparation RF pulse.

19. The method as recited in claim 1, wherein the selected magnetization state is one of a pulsed steady-state, a thermal equilibrium, or a desired level of saturation.

20. The method as recited in claim 1, wherein step (e) includes reconstructing the images using an iterative reconstruction that is regularized in part using a multi-scale locally low-rank noise reduction.

21. The method as recited in claim 1, wherein step (e) includes reconstructing the images using an iterative reconstruction that is regularized in part using a low-rank tensor regularization.

* * * * *